(12) United States Patent
Stirton et al.

(10) Patent No.: US 6,881,594 B1
(45) Date of Patent: Apr. 19, 2005

(54) METHOD OF USING SCATTEROMETRY FOR ANALYSIS OF ELECTROMIGRATION, AND STRUCTURES FOR PERFORMING SAME

(75) Inventors: James Broc Stirton, Austin, TX (US);
Steven P. Reeves, Austin, TX (US);
Homi E. Nariman, Austin, TX (US);
Kevin R. Lensing, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 183 days.

(21) Appl. No.: 10/281,666

(22) Filed: Oct. 28, 2002

(51) Int. Cl.[7] .............................................. H01L 21/00
(52) U.S. Cl. ......................................... 438/14; 438/468
(58) Field of Search ............................. 438/14, 16–18, 438/466, 468; 702/155, 167, 172

(56) References Cited

U.S. PATENT DOCUMENTS

| | | | |
|---|---|---|---|
| 5,867,276 A | 2/1999 | McNeil et al. | 356/445 |
| 5,877,860 A | 3/1999 | Borden | 356/376 |
| 5,880,838 A | 3/1999 | Marx et al. | 356/351 |
| 6,051,348 A | 4/2000 | Marinaro et al. | 430/30 |
| 6,081,334 A | 6/2000 | Grimbergen et al. | 356/357 |
| 6,245,584 B1 | 6/2001 | Marinaro et al. | 438/14 |
| 6,433,878 B1 | 8/2002 | Niu et al. | 356/603 |
| 2002/0135781 A1 | 9/2002 | Singh et al. | 356/601 |

*Primary Examiner*—Evan Pert
(74) *Attorney, Agent, or Firm*—Williams, Morgan & Amerson, P.C.

(57) ABSTRACT

The present invention is generally directed to various methods of using scatterometry for analysis of electromigration. In one illustrative embodiment, the method comprises forming a grating structure above a semiconducting substrate, the grating structure being comprised of a plurality of conductive structures, forcing an electrical current through at least one of the conductive structures and performing scatterometric measurements of at least one conductive structure to detect a change in shape of at least a portion of the conductive structure. In further embodiments, the method comprises determining a susceptibility of at least one conductive structure to electromigration based upon the detected change in shape of the conductive structure.

54 Claims, 4 Drawing Sheets

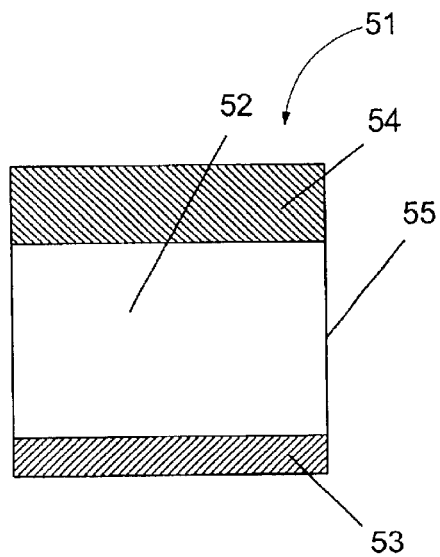
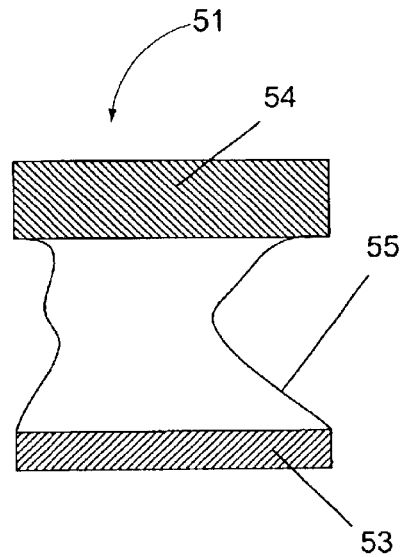
Figure 5A       Figure 5B
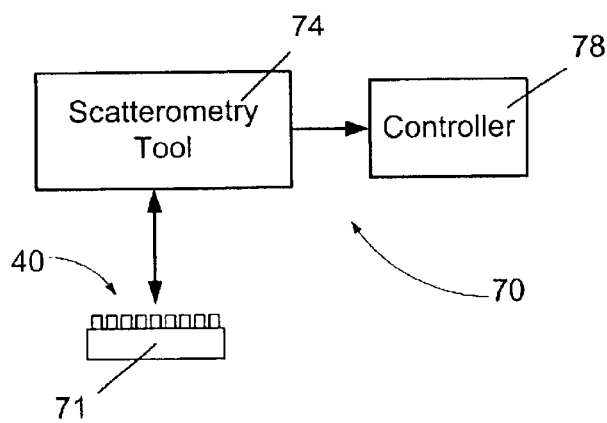
Figure 6

METHOD OF USING SCATTEROMETRY FOR ANALYSIS OF ELECTROMIGRATION, AND STRUCTURES FOR PERFORMING SAME

BACKGROUND OF THE INVENTION

1. Field of the Invention

This invention relates generally to semiconductor fabrication technology, and, more particularly, to methods of using scatterometry for analysis of electromigration, and structures for performing same.

2. Description of the Related Art

By way of background, modern integrated circuit devices, e.g., microprocessors, ASICs, memory devices, etc., are comprised of millions of field effect transistors formed on a semiconducting substrate, such as silicon. The substrate may be doped with either N-type or P-type dopant materials. An illustrative field effect transistor 10, as shown in FIG. 1, may have a doped polycrystalline silicon (polysilicon) gate electrode 14 formed above a gate insulation layer 16. The gate electrode 14 and the gate insulation layer 16 may be separated from doped source/drain regions 22 of the transistor 10 by a dielectric sidewall spacer 20. The source/drain regions 22 for the transistor 10 may be formed by performing one or more ion implantation processes to introduce dopant atoms, e.g., arsenic or phosphorous for NMOS devices, boron for PMOS devices, into the substrate 11. Shallow trench isolation regions 18 may be provided to isolate the transistor 10 electrically from neighboring semiconductor devices, such as other transistors (not shown). Additionally, although not depicted in FIG. 1, a typical integrated circuit product is comprised of a plurality of conductive interconnections, such as conductive lines and conductive contacts or vias, positioned in multiple layers of insulating material formed above the substrate. These conductive interconnections allow electrical signals to propagate between the transistors formed above the substrate.

The gate electrode 14 has a critical dimension 12, i.e., the width of the gate electrode 14, that approximately corresponds to the channel length 13 of the device when the transistor 10 is operational. Of course, the critical dimension 12 of the gate electrode 14 is but one example of a feature that must be formed very accurately in modern semiconductor manufacturing operations. Other examples include, but are not limited to, conductive lines, openings in insulating layers to allow subsequent formation of a conductive interconnection, i.e., a conductive line or contact, therein, etc.

As device dimensions have continued to shrink, the packing density of the semiconductor devices, e.g., transistors, has increased. That is, ever increasing numbers of transistors or memory cells are located on the same plot space of a semiconducting substrate. As a result of this increased device density, the conductive metal lines and contacts or vias that connect these various devices have also been reduced in physical size, and they are also packed more closely together. In general, the resistance of a metal line is inversely proportional to the cross-sectional area of the metal line. Thus, all other things being equal, it is important that the cross-sectional area of the metal line be maintained above certain minimum levels such that the resistance of the metal line does not exceed allowable limits. Unanticipated increases in the resistance of a metal line may adversely impact device performance, e.g., a reduction in operating frequency, increased heat build-up, increased power consumption, etc.

Unfortunately, a phenomenon known as electromigration can adversely impact conductive metal lines in an integrated circuit product. In general, electromigration is a process whereby a conductive structure, such as a metal line, contact or via, tends to degrade, thereby resulting in a change in the physical characteristics, e.g., shape, size, etc., of the conductive structure. Typically, electromigration occurs when a current is passed through relatively long conductive structures. The current sets up an electrical field in the conductive structure that decreases from the input side to the output side of the conductive structure. Additionally, heat generated by the flowing current sets up a thermal gradient along the conductive structure. As a result, the metal atoms in the conductive structure become mobile and diffuse within the conductive structure. This electromigration phenomenon results in physical changes to the size and/or shape of the conductive structure. For example, in some cases, the conductive structure may be thinned at one or more locations. In a worst case scenario, electromigration can cause complete separation of the conductive structure. This electromigration phenomenon can occur on metals such as aluminum, copper, tungsten and titanium.

In designing integrated circuit products, efforts are taken to reduce, eliminate or account for electromigration of conductive structures in integrated circuit products. Such efforts may include selecting appropriate materials, making conductive structures sufficiently large such that the effects of electromigration do not adversely impact the performance of the integrated circuit product over its useful life.

Typically, one or more tests are performed on an integrated circuit product to determine its ability to withstand electromigration during the product lifetime. FIG. 2 shows an illustrative test structure 30 that can be used for such purposes. The test structure 30 is comprised of a conductive metal line 32, a plurality of dummy metal lines 34, and contacts 36 coupled to each end of the conductive metal line 32. The lines 32, 34 have a layer of insulating material 38 positioned therebetween. A relatively high current, much higher than that anticipated in normal usage of the integrated circuit product, is passed through the conductive metal line 32 until such time as the resistance of the conductive metal line 32 increases by a preselected amount, e.g., 10% or 20%. The increase in resistance is due to material loss and/or change in shape of the conductive metal line 32 due to electromigration. The acceptability of the product as to its ability to withstand electromigration depends upon the time it takes for the conductive metal line to exhibit the established standard for increase in resistance. Such testing can be very time-consuming. For example, such an electromigration test may involve subjecting the conductive metal line 32 to the test current for 10–12 hours.

Additionally, electromigration testing as described above tends to produce very sharp changes in resistance. That is, the resistance measurements tend to degrade rather slowly and fall rapidly over a short period of time, i.e., the measurements exhibit a cliff-like characteristic. This is especially true in cases where various cap layers (not shown), e.g., titanium, titanium-nitride, are positioned above and/or below the conductive metal line. In such a structure, the cap layers tend to carry a very high percentage, e.g., 70–90%, of the total current. Thus, the detection of erosion or change in shape of the conductive metal line 32 positioned between the cap layers may not be readily ascertained based on the electrical test data alone.

The present invention is directed to various methods and structures that may solve, or at least reduce, some or all of the aforementioned problems.

SUMMARY OF THE INVENTION

The present invention is generally directed to scatterometry structures designed for analysis of electromigration, and methods of using same. In one illustrative embodiment, the method comprises forming a grating structure above a semiconducting substrate, the grating structure being comprised of a plurality of conductive structures, forcing an electrical current through at least one of the conductive structures and performing scatterometric measurements of at least one conductive structure to detect a change in shape of at least a portion of the conductive structure. The method further comprises determining a susceptibility of at least one conductive structure to electromigration based upon the detected change in shape of the conductive structure.

BRIEF DESCRIPTION OF THE DRAWINGS

The invention may be understood by reference to the following description taken in conjunction with the accompanying drawings, in which like reference numerals identify like elements, and in which:

FIGS. 5A–5B are cross-sectional views of another illustrative embodiment of a conductive structure that comprises a grating structure that may be employed with the present invention; and FIG. 6 is a schematic depiction of an illustrative system that may be employed with the present invention.

Figure 1:
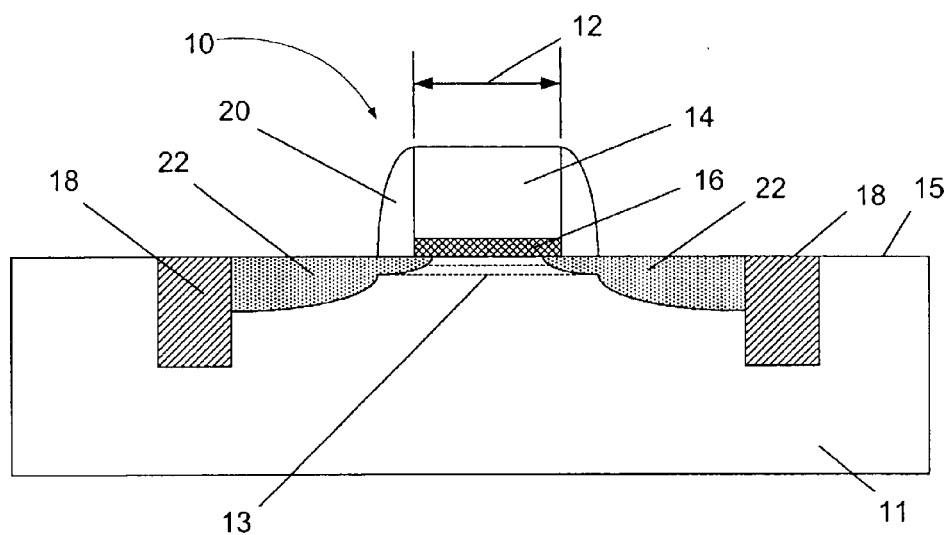
FIG. 1 is a cross-sectional view of an illustrative prior art transistor.
Figure 2:
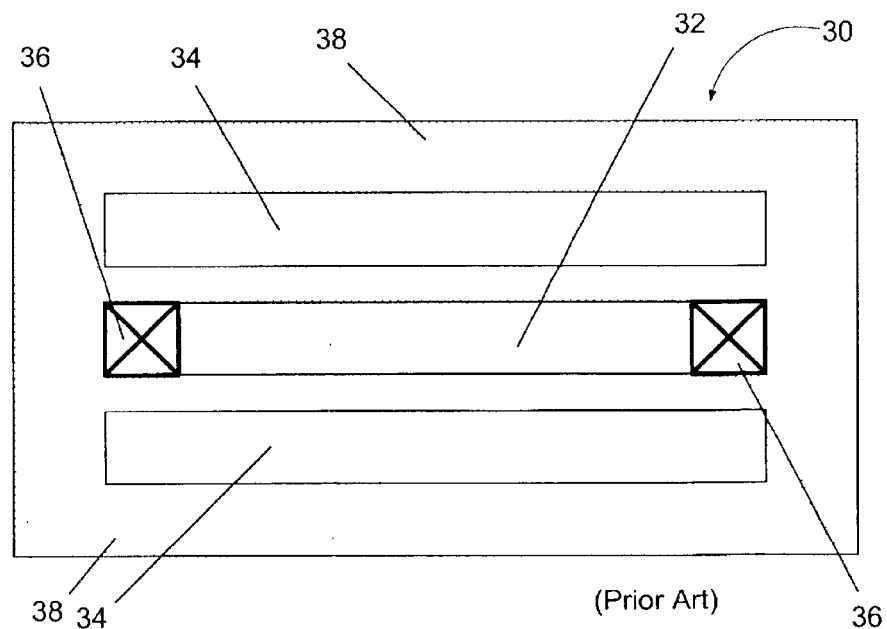
FIG. 2 is a plan view of an illustrative prior art structure employed in electromigration testing.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device are depicted in the drawings as having very precise, sharp configurations and profiles, those skilled in the art recognize that, in reality, these regions and structures are not as precise as indicated in the drawings. Additionally, the relative sizes of the various features and doped regions depicted in the drawings may be exaggerated or reduced as compared to the size of those features or regions on fabricated devices. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In general, the present invention is directed to various methods of using scatterometry for analysis of electromigration, and structures and systems for performing same. As will be readily apparent to those skilled in the art upon a complete reading of the present application, the present method is applicable to a variety of technologies, e.g., NMOS, PMOS, CMOS, etc., and it is readily applicable to a variety of devices, including, but not limited to, logic devices, memory devices, etc. Moreover, the present methods may be employed to test the electromigration characteristics of a variety of conductive structures.

Figure 3A:
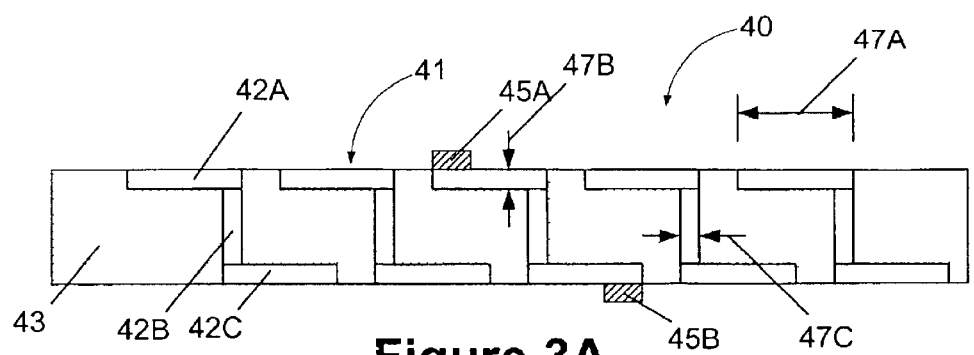
FIGS. 3A–3C depict one illustrative embodiment of a grating structure that may be employed with the present invention.
Figure 3B:
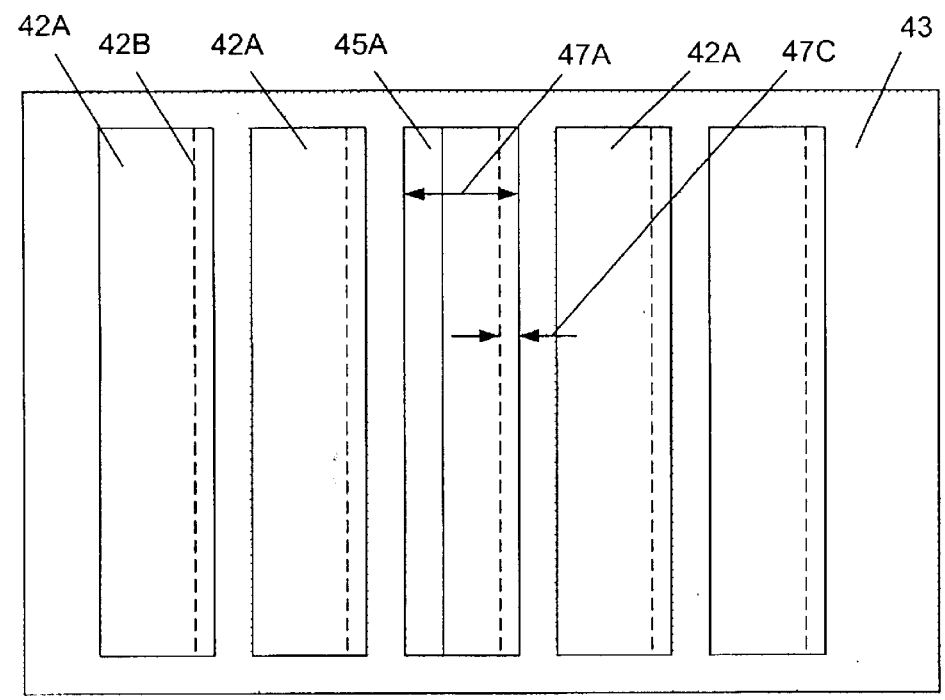
Figure 3C:
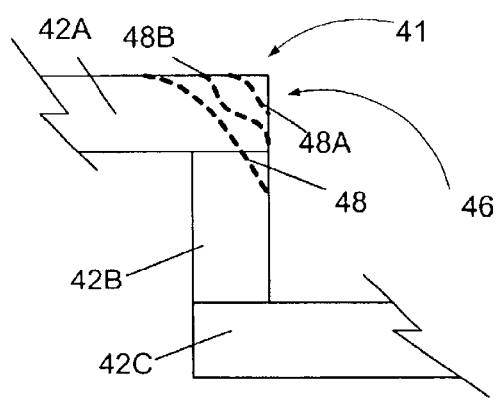

In one aspect, the present invention is generally directed to performing electromigration analysis by using scatterometry-based metrology to measure a grating structure. FIGS. 3A–3C depict one illustrative embodiment of a grating structure 40 that may be employed with the present invention. As shown therein, the grating structure 40 is comprised of a plurality of conductive structures 41 positioned in a layer of insulating material 43, such as silicon dioxide. The size, shape and configuration of the conductive structures 41 may vary. In the depicted embodiment in FIGS. 3A–3C, the conductive structure 41 is comprised of a top conductive line 42A, a conductive contact 42B, and a bottom conductive line 42C. Conductive contacts 45A and 45B are coupled to the conductive structures 41 in the middle. The outside conductive structures 41 (two on each side of the middle conductive structures 41) are essentially dummy structures in the depicted embodiment. The grating structure 40 may be formed as a separate test structure, or in some embodiments, it may be comprised of features, e.g., metal lines, that are part of actual production devices. For example, the grating structure 40 may be essentially a test structure that is formed in an area defined by an unused area or a scribe line of a wafer. In the case of actual production devices, the conductive structures 41 that comprise the grating structure 40 may be a plurality of conductive metal lines that are part of the completed integrated circuit product.

The size and shape of the conductive structures 41 in the grating structure 40 may vary. In one illustrative embodiment, the top and bottom conductive lines 42A, 42C have a width 47A of approximately 0.4–0.6 μm and a thickness 47B of approximately 0.18–0.25 μm. In the depicted embodiment, the contacts 42B extend for approximately the full length of the conductive lines 42A/42C, i.e., into the drawing page. These conductive contacts 42C have a thickness 47C that ranges from approximately 0.18–0.25 μm.

The number of conductive structures 41 that comprise the grating structure 40 may also vary. For example, the grating structure 40 may occupy approximately 100 μm×100 μm (10,000 μm$^2$) of surface area, and approximately 100–700 conductive structures 41 may be part of the grating structure 40. For ease of explanation, only five representative conductive structures 41 are depicted in FIGS. 3A–3C. As will be recognized by those skilled in the art after a complete reading of the present application, the size, shape and number of conductive structures 41 that make up the grating structure 40 should not be considered a limitation of the present invention unless such limitations are expressly set forth in the appended claims. Additionally, the conductive structures 41 may be comprised of a variety of materials or combination of materials. For example, the conductive structure 41 may be comprised of aluminum, copper, tungsten, titanium, etc. One or more capping layers, e.g., titanium, titanium nitride, maybe positioned adjacent at least portions of the conductive structure 41.

Figure 4A:
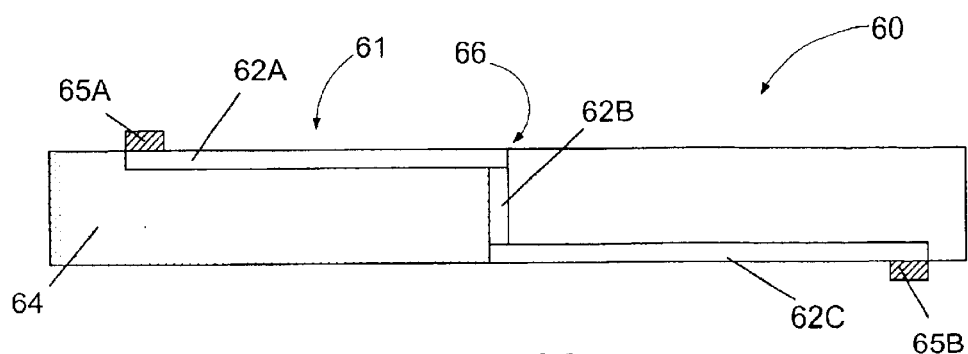
FIGS. 4A–4B depict an embodiment of another illustrative grating structure that may be employed with the present invention.
Figure 4B:
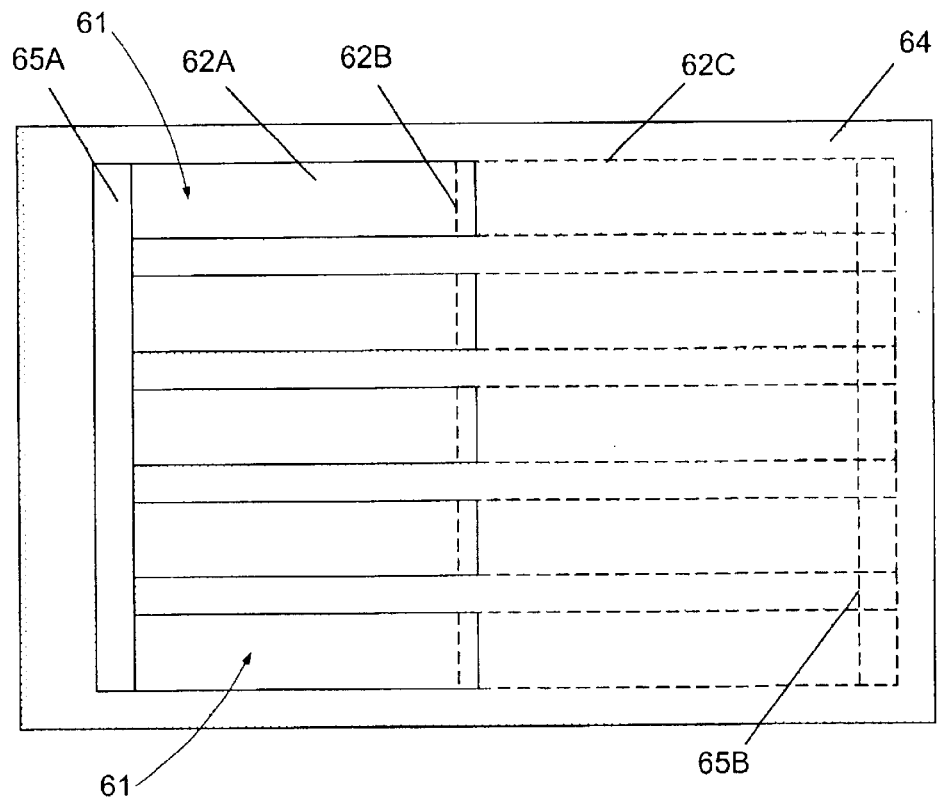

FIGS. 4A–4B depict another illustrative embodiment of a grating structure 60 that may be employed with the present invention. As shown therein, the grating structure 60 is comprised of a plurality of conductive structures 61. In the depicted embodiment, the conductive structures 61 are comprised of a top conductive line 62A, a bottom conductive line 62C and a conductive contact 62B. A layer of insulating material 64 is positioned around the various conductive members 61. A contact bar 65A is coupled to the top conductive lines 62A, and a contact bar 65B is coupled to the bottom conductive lines 62C.

FIGS. 5A–5B are cross-sectional views of another embodiment of a conductive structure 51 that may be employed in the context of the present invention. The conductive structure 51 depicted in FIG. 5A is essentially a conductive metal line that is comprised of an aluminum line 52, a bottom cap layer 53 and a top cap layer 54. The bottom cap layer 53 may be comprised of, for example, titanium nitride, having a thickness of approximately 25–35 nm. The top cap layer 54 may actually be a dual layer system (not shown in Figures 5A–5B) comprised of, for example, titanium/titanium nitride, and it may have an overall thickness of approximately 30–75 nm. The aluminum line 52 may have a thickness of approximately 250–500 nm. A grating structure that may be employed with the present invention may be comprised of a plurality of the conductive structures 51. As initially formed, the conductive structure 51 may have a cross-sectional configuration like that depicted in FIG. 5A, i.e., rectangular with relatively vertical sidewalls 55. However, due to electromigration, the aluminum line 52 may erode or change shape as indicated in FIG. 5B.

In general, electromigration effects will be analyzed by performing scatterometric measurements of a grating structure. Electromigration causes a change in the shape of a conductive structure 41, 51, 61 over time. This is due to material loss and/or migrating of the material over time. FIG. 3C is an enlarged view of a portion of one of the conductive structures 41 that comprise the grating structure 40 shown in FIGS. 3A–3C. As shown therein, the conductive structure 41 begins with an approximately square-edged corner region 46. However, due to the effects of electromigration, the corner region 46 may erode or change shape such that the corner region 46 exhibits a profile or shape like that depicted by the dashed line 48. The change in shape of the conductive structure 41 is usually very gradual in nature. That is, the electromigration causes the shape of the conductive structure 41 to progressively change from that indicated by dashed line 48A to that of line 48B to that of line 48. This process may continue until the device actually fails, i.e., until there is a physical separation of the conductive member 41. As stated previously, the conductive structure 51 depicted in FIGS. 5A–5B may also exhibit the effects of electromigration.

The change in shape of the conductive structures due to electromigration can be detected by scatterometric measurements. Of course, virtually any portion of a conductive structure may be subjected to a change in size and/or shape due to electromigration. Thus, the selection of the illustrative corner region 46 in FIG. 3C for purposes of discussing the present invention should not be considered a limitation of the present invention unless such limitations are clearly set forth in the appended claims. Moreover, the discussion regarding the change of shape of the conductive structure 41 applies equally to the conductive structure 61 depicted in FIGS. 4A–4B. Lastly, it should also be understood that the term "conductive structures" is intended to be used in a generic sense, i.e., one that is not limited to any particular shape or configuration. For example, the conductive structures of the present invention may take the form of the illustrative conductive structures 41, 51, 61 depicted herein, or any other configuration.

An illustrative system 70 that may be used in one embodiment of the present invention is shown in FIG. 6. The system 70 is comprised of a scatterometry tool 74 and a controller 78. As indicated in FIG. 6, the wafer 71 is representative of one or more wafers having a grating structure, e.g., the grating structure 40, formed thereabove.

A variety of scatterometry tools 74 may be used with the present invention, e.g., so-called 2θ-type systems and lens-type scatterometry tools. The scatterometry tool 74 is comprised of, among other things, a light source (not shown) and a collector (not shown). The scatterometry tool 74 may use white light, or some other wavelength or combination of wavelengths, depending on the specific implementation. Typically, the scatterometry tool 74 will generate an incident beam that has a wide spectral composition and wherein the intensity of the light changes slowly in comparison to changes in wavelength. The angle of incidence of the light may also vary, depending on the specific implementation. The light analyzed by the scatterometry tool 74 typically includes a reflected component (i.e., incident angle equals reflected angle) and a refracted component (i.e., incident angle does not equal the reflected angle). For purposes of discussion hereinafter, the term "reflected" light is meant to encompass both components. The optical characteristic trace generated by the scatterometry tool 74 may be based upon a comparison of light intensity to wavelength (for white light, fixed angle type scatterometry tools) or a comparison of intensity to incident angle (for angle resolved systems that use a single light source). The optical characteristic traces may be based upon any aspect of a reflection profile (e.g., intensity vs. wavelength—tan(δ), phase vs. wavelength—sin(ψ), where δ and ψ are common scatterometry outputs known to those of ordinary skill in the art).

In general, the scatterometry tool 74 includes optical hardware, such as an ellipsometer or reflectometer, and a data processing unit loaded with a scatterometry software application for processing data collected by the optical hardware. For example, the optical hardware may include a Model OP5230 or OP5240 with a spectroscopic ellipsometer offered by Thermawave, Inc. of Fremont, Calif. The data processing unit may comprise a profile application server manufactured by Timbre Technologies, a fully owned subsidiary of Tokyo Electron America, Inc. of Austin, Tex. and distributed by Thermawave, Inc. Scatterometry libraries are commercially available from Timbre Technologies, Inc.

In the illustrated embodiments, the controller 78 is a computer programmed with software to implement the functions described herein. Moreover, the functions described for the controller 78 may be performed by one or more controllers spread through the system. For example, the controller 78 may be a fab level controller that is used to control processing operations throughout all or a portion of a semiconductor manufacturing facility. Alternatively, the controller 78 may be a lower level computer that controls only portions or cells of the manufacturing facility. Moreover, the controller 78 may be a stand-alone device, or it may reside on the scatterometry tool 74. However, as will be appreciated by those of ordinary skill in the art, a hardware controller (not shown) designed to implement the particular functions may also be used.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the controller 64, as described, is the Catalyst system offered by KLA Tencor, Inc. The Catalyst system uses Semiconductor Equipment and Materials International (SEMI) Computer Integrated Manufacturing (CIM) Framework compliant system technologies, and is based on the Advanced Process Control (APC) Framework. CIM (SEMI E81-0699—Provisional Specification for CIM Framework Domain Architecture) and APC (SEMI E93-0999—Provisional Specification for CIM Framework Advanced Process Control Component) specifications are publicly available from SEMI.

Through use of the present invention, an optical characteristic trace may be established for a vast variety, if not all, anticipated shapes or profiles of the conductive structures 41, 51, 61 after they have been subjected to varying degrees of degradation due to electromigration. The optical characteristic trace may be generated using a variety of optical metrology tools to be discussed more fully below. A library of optical characteristic traces corresponding to each unique anticipated shape or profile of the conductive structures 41, 51, 61 subjected to erosion due to electromigration may be calculated (using Maxwell's equations). Obviously, the number of combinations used to create the library may vary as a matter of design choice. Moreover, the greater the number of combinations, the greater will be the library containing the appropriate signature profiles of the eroded conductive structures. This library of traces may be stored in a database that is readily accessible by the controller 78 and/or the scatterometry tool 74.

The scatterometry tool 74 may be used to measure one or more of the conductive structures that comprise the grating structure. As a result, an optical characteristic trace associated with this measurement may be generated. This generated optical characteristic trace will then be compared or correlated to optical characteristic traces in the library containing probable known configurations or shape of the conductive structure to determine the best fit or match. Based upon this comparison or correlation, the measured conductive structure is determined to have a shape that corresponds to or closely approximates that of conductive structures associated with the matched optical characteristic trace from the library.

The present invention may be employed in a variety of contexts. For example, the scatterometric measurements of the present invention may be performed as electrical current is being forced through the conductive structures, or after the current has been stopped. Moreover, the particular test protocol may vary. For example, a current may be forced through the grating structures for a period of time, the current may then be stopped, and one or more scatterometric measurements may then be performed. Thereafter, electrical current may again be applied to the grating structure, and the process may continue until such time as the electromigration testing is completed. The magnitude of the current used for the electromigration analysis will vary depending upon the particular application.

By use of scatterometric techniques, the shape of the conductive structure may be determined and used to determine the ability of the conductive structure to withstand electromigration. In some cases, the use of scatterometry may be used to reduce the time required for testing for electromigration. Over time, data may be acquired as to the change in shape of a conductive structure as a result of a relatively long electromigration test. For devices that are acceptable, the change in shape of the conductive structure during the testing may be determined.

Through use of the present invention, the shape of the conductive structure relatively early during the electromigration testing may be measured using scatterometry to determine the susceptibility of the conductive structure to electromigration. Stated another way, if the shape of the conductive structure has not degraded beyond a certain point at a specific time during the electromigration testing protocol, then, based upon historical data, it can be assumed that the devices being tested will likewise pass the electromigration test.

Conversely, the method of the present invention may be used relatively early in the testing process to identify and detect devices that are going to fail the electromigration test. That is, if the change in shape of the conductive structure exceeds a certain amount at a particular point in a given testing protocol, then it may be reasonably assumed that the device will fail the electromigration test.

Additionally, the present invention may be used to determine a rate of change of the size or shape of the conductive structure due to electromigration. That is, the degradation in the shape of the conductive structure may be determined after the conductive structure has been subjected to the test current for a specified period of time. Using scatterometry, the shape of the conductive structure may be determined before and after this testing period. Based upon this information, the rate of change in the shape of the conductive structures may be determined and used to determine and/or predict the conductive structures' susceptibility to electromigration. The rate of change of the conductive structure over time may be expressed in any convenient means, e.g., a percentage loss of area per unit time.

In one aspect, the present invention is generally directed to various methods of using scatterometry for analysis of electromigration. In one illustrative embodiment, the method comprises forming a grating structure above a semiconducting substrate, the grating structure being comprised of a plurality of conductive structures, forcing an electrical current through at least one of the conductive structures and performing scatterometric measurements of at least one conductive structure to detect a change in shape of at least a portion of the conductive structure. The method further comprises determining a susceptibility of at least one conductive structure to electromigration based upon the detected change in shape of the conductive structure.

By use of the present invention, electromigration analysis may be accomplished in a more timely fashion. Moreover, the scatterometry-based techniques described herein may provide more sensitive feedback as to the actual physical effects of electromigration on a conductive structure. That is, by determining the change in shape of the conductive structure, relatively small changes in the shape of a conductive structure may be readily determined.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method of performing electromigration analysis, comprising:
   forming a grating structure above a semiconducting substrate, said grating structure being comprised of a plurality of conductive structures;
   forcing an electrical current through at least one of said conductive structures; and
   performing scatterometric measurements of said at least one conductive structure to detect a change in shape of at least a portion of said at least one conductive structure.

2. The method of claim 1, wherein said conductive structures are conductive metal lines.

3. The method of claim 1, wherein each of said conductive structures is comprised of a conductive metal line and at least one cap layer positioned above and below said conductive metal line.

4. The method of claim 1, wherein each of said conductive structures is comprised of a first metal line and a second metal line that are spaced apart from one another by a conductive contact that is conductively coupled to each of said first and second metal lines.

5. The method of claim 1, wherein each of said conductive structures is comprised of at least one of aluminum, copper, tungsten and titanium.

6. The method of claim 1, wherein said grating structure occupies approximately 10,000 $\mu m^2$ of surface area.

7. The method of claim 1, wherein said grating structure is comprised of approximately 100–700 conductive structures.

8. The method of claim 1, wherein performing scatterometric measurements comprises illuminating said at least one conductive structure and measuring light reflected therefrom.

9. The method of claim 1, wherein said scatterometric measurements are performed on at least a corner region of said at least one conductive structure.

10. The method of claim 1, further comprising determining a susceptibility of said at least one conductive structure to electromigration based upon said detected change in shape of said at least one conductive structure.

11. The method of claim 1, wherein said scatterometric measurements are performed while said electrical current is being forced through said at least one conductive structure.

12. The method of claim 1, wherein said scatterometric measurements are performed after stopping said electrical current.

13. The method of claim 1, further comprising determining a rate of change of said shape of said at least one conductive structure and using said determined rate of change of said shape of said at least one conductive structure to predict the susceptibility of said at least one conductive structure to electromigration.

14. A method of performing electromigration analysis, comprising:
   forming a grating structure above a semiconducting substrate, said grating structure being comprised of a plurality of conductive structures;
   forcing an electrical current through at least one of said conductive structures;
   performing scatterometric measurements of said at least one conductive structure while said electrical current is being forced through said at least one conductive structure to detect a change in shape of at least a portion of said at least one conductive structure; and
   determining a susceptibility of said at least one conductive structure to electromigration based upon said detected change in shape of said at least one conductive structure.

15. The method of claim 14, wherein said conductive structures are conductive metal lines.

16. The method of claim 14, wherein each of said conductive structures is comprised of a conductive metal line and at least one cap layer positioned above and below said conductive metal line.

17. The method of claim 14, wherein each of said conductive structures is comprised of a first metal line and a second metal line that are spaced apart from one another by a conductive contact that is conductively coupled to each of said first and second metal lines.

18. The method of claim 14, wherein each of said conductive structures is comprised of at least one of aluminum, copper, tungsten and titanium.

19. The method of claim 14, wherein said grating structure occupies approximately 10,000 $\mu m^2$ of surface area.

20. The method of claim 14, wherein said grating structure is comprised of approximately 100–700 conductive structures.

21. The method of claim 14, wherein performing scatterometric measurements comprises illuminating said at least one conductive structure and measuring light reflected therefrom.

22. The method of claim 14, wherein said scatterometric measurements are performed on at least a corner region of said conductive structure.

23. The method of claim 14, further comprising determining a rate of change of said shape of said at least one conductive structure and using said determined rate of change of said shape of said at least one conductive structure to predict the susceptibility of said at least one conductive structure to electromigration.

24. A method of performing electromigration analysis, comprising:

forming a grating structure above a semiconducting substrate, said grating structure being comprised of a plurality of conductive structures;

forcing an electrical current through at least one of said conductive structures;

after stopping said electrical current, performing scatterometric measurements of said at least one conductive structure to detect a change in shape of at least a portion of said at least one conductive structure; and determining a susceptibility of said at least one conductive structure to electromigration based upon said detected change in shape of said at least one conductive structure.

25. The method of claim 24, wherein said conductive structures are conductive metal lines.

26. The method of claim 24, wherein each of said conductive structures is comprised of a conductive metal line and at least one cap layer positioned above and below said conductive metal line.

27. The method of claim 24, wherein each of said conductive structures is comprised of a first metal line and a second metal line that are spaced apart from one another by a conductive contact that is conductively coupled to each of said first and second metal lines.

28. The method of claim 24, wherein each of said conductive structures is comprised of at least one of aluminum, copper, tungsten and titanium.

29. The method of claim 24, wherein said grating structure occupies approximately 10,000 $\mu m^2$ of surface area.

30. The method of claim 24, wherein said grating structure is comprised of approximately 100–700 conductive structures.

31. The method of claim 24, wherein performing scatterometric measurements comprises illuminating said at least one conductive structure and measuring light reflected therefrom.

32. The method of claim 24, wherein said scatterometric measurements are performed on at least a corner region of said conductive structure.

33. The method of claim 24, further comprising determining a rate of change of said shape of said at least one conductive structure and using said determined rate of change of said shape of said at least one conductive structure to predict the susceptibility of said at least one conductive structure to electromigration.

34. A method of performing electromigration analysis, comprising:

forming a grating structure above a semiconducting substrate, said grating structure being comprised of a plurality of conductive structures;

forcing an electrical current through at least one of said conductive structures;

performing scatterometric measurements of said at least one conductive structure to detect a change in shape of at least a portion of said at least one conductive structure; and determining a rate of change of said shape of said at least one conductive structure and using said determined rate of change of said shape of said at least one conductive structure to predict the susceptibility of said at least one conductive structure to electromigration.

35. The method of claim 34, wherein said conductive structures are conductive metal lines.

36. The method of claim 34, wherein each of said conductive structures is comprised of a conductive metal line and at least one cap layer positioned above and below said conductive metal line.

37. The method of claim 34, wherein each of said conductive structures is comprised of a first metal line and a second metal line that are spaced apart from one another by a conductive contact that is conductively coupled to each of said first and second metal lines.

38. The method of claim 34, wherein each of said conductive structures is comprised of at least one of aluminum, copper, tungsten and titanium.

39. The method of claim 34, wherein said grating structure occupies approximately 10,000 $\mu m^2$ of surface area.

40. The method of claim 34, wherein said grating structure is comprised of approximately 100–700 conductive structures.

41. The method of claim 34, wherein performing scatterometric measurements comprises illuminating said at least one conductive structure and measuring light reflected therefrom.

42. The method of claim 34, wherein said scatterometric measurements are performed on at least a corner region of said conductive structure.

43. The method of claim 34, wherein said scatterometric measurements are performed while said electrical current is being forced through said at least one conductive structure.

44. The method of claim 34, wherein said scatterometric measurements are performed after stopping said electrical current.

45. A method of performing electromigration analysis, comprising:

forming a grating structure above a semiconducting substrate, said grating structure being comprised of a plurality of aluminum conductive structures;

forcing an electrical current through at least one of said conductive structures;

performing scatterometric measurements of said at least one conductive structure to detect a change in shape of at least a portion of said at least one conductive structure; and determining a susceptibility of said at least one conductive structure to electromigration based upon said detected change in shape of said at least one conductive structure.

46. The method of claim 45, wherein each of said conductive structures is comprised of a conductive metal line and at least one cap layer positioned above and below said conductive metal line.

47. The method of claim 45, wherein each of said conductive structures is comprised of a first metal line and a second metal line that are spaced apart from one another by a conductive contact that is conductively coupled to each of said first and second metal lines.

48. The method of claim 45, wherein said grating structure occupies approximately 10,000 $\mu m^2$ of surface area.

49. The method of claim 45, wherein said grating structure is comprised of approximately 100–700 conductive structures.

50. The method of claim 45, wherein performing scatterometric measurements comprises illuminating said at least one conductive structure and measuring light reflected therefrom.

51. The method of claim 45, wherein said scatterometric measurements are performed on at least a corner region of said conductive structure.

52. The method of claim 45, wherein said scatterometric measurements are performed while said electrical current is being forced through said at least one conductive structure.

53. The method of claim 45, wherein said scatterometric measurements are performed after stopping said electrical current.

54. The method of claim 45, further comprising determining a rate of change of said shape of said at least one conductive structure and using said determined rate of change of said shape of said at least one conductive structure to predict the susceptibility of said at least one conductive structure to electromigration.

* * * * *